United States Patent
Haartsen et al.

(10) Patent No.: US 8,705,784 B2
(45) Date of Patent: Apr. 22, 2014

(54) ACOUSTIC IN-EAR DETECTION FOR EARPIECE

(75) Inventors: Jacobus Cornelis Haartsen, BG Hardenberg (NL); Gerrit Sampimon, PV Erm (NL); Bart Trip, GA Emmen (NL)

(73) Assignees: Sony Corporation, Tokyo (JP); Sony Mobile Communications AB, Lund (SE)

( * ) Notice: Subject to any disclaimer, the term of this patent is extended or adjusted under 35 U.S.C. 154(b) by 811 days.

(21) Appl. No.: 12/358,285

(22) Filed: Jan. 23, 2009

(65) Prior Publication Data

US 2010/0189268 A1 Jul. 29, 2010

(51) Int. Cl.
 *H04R 25/00* (2006.01)

(52) U.S. Cl.
 USPC .......................................... 381/328; 381/380

(58) Field of Classification Search
 USPC ..... 381/310, FOR. 126, FOR. 133, 323, 312, 381/328, 330, 370, 380, 381, 384; 607/6; 600/301, 322–324, 340, 483, 485, 500, 600/508, 528, 559
 See application file for complete search history.

(56) References Cited

U.S. PATENT DOCUMENTS

| | | | |
|---|---|---|---|
| 6,277,079 B1 * | 8/2001 | Avicola et al. | 600/502 |
| 6,415,034 B1 * | 7/2002 | Hietanen | 381/71.6 |
| 2004/0037428 A1 * | 2/2004 | Keller | 381/60 |
| 2004/0196992 A1 * | 10/2004 | Ryan | 381/312 |
| 2006/0013079 A1 | 1/2006 | Rekimoto | 369/30.01 |
| 2007/0009122 A1 * | 1/2007 | Hamacher | 381/312 |
| 2008/0089530 A1 | 4/2008 | Bostick et al. | |
| 2008/0123882 A1 | 5/2008 | Bauml et al. | |
| 2008/0146890 A1 | 6/2008 | LeBoeuf et al. | 600/300 |
| 2008/0298606 A1 | 12/2008 | Johnson et al. | |
| 2009/0105548 A1 * | 4/2009 | Bart | 600/300 |
| 2009/0124286 A1 * | 5/2009 | Hellfalk et al. | 455/556.1 |
| 2009/0259116 A1 * | 10/2009 | Wasserman et al. | 600/323 |

FOREIGN PATENT DOCUMENTS

| | | |
|---|---|---|
| EP | 1 594 344 | 11/2005 |
| JP | 2004-297256 | 10/2004 |
| JP | 2006-024241 | 1/2006 |
| JP | 2007-165940 | 6/2007 |
| JP | 2008-219586 | 9/2008 |

OTHER PUBLICATIONS

International Search Report for corresponding international application No. PCT/EP2009/059193 dated Oct. 26, 2009.
Written Opinion for corresponding international application No. PCT/EP2009/059193 dated Oct. 26, 2009.

* cited by examiner

*Primary Examiner* — Brian Ensey
(74) *Attorney, Agent, or Firm* — Renner, Otto, Boisselle & Sklar, LLP

(57) ABSTRACT

An apparatus comprising an earpiece and a signal processor is disclosed. The earpiece is suitable to be applied at an auditory opening of a user's ear. The earpiece comprises a speaker enabled to be supplied with an audio signal for rendering, and a microphone arranged in vicinity of the speaker to acquire a sound signal from sounds present inside the auditory opening when the earpiece is applied at the ear. The signal processor is arranged to determine whether the earpiece is applied at the user's ear by analysis of the acquired sound signal comprising any of a sound signal component of an in-ear sound type present when the earpiece is applied or an outside-ear sound type present when the earpiece is not applied. A method and a computer program are also disclosed.

31 Claims, 2 Drawing Sheets

ACOUSTIC IN-EAR DETECTION FOR EARPIECE

TECHNICAL FIELD

The present invention relates to an apparatus, a method, and a computer program for detecting application of an earpiece. In particular, the invention relates to detection of the application made from an acquired sound signal.

BACKGROUND

Devices utilizing earphones, wired or wireless, for providing speech, music, etc. to a user have become popular. Such devices can be portable media players, mobile telephones, and portable digital assistants. Detection of whether the earphone is in listening position, i.e. applied at the ear, has been utilized for reducing power consumption when the user is not able to listen to any provided audio content. For example in US 2006/0045304 A1, it is disclosed that a detection element comprising two electrodes on an outer surface of the earphone body such that when the earphone is applied at the ear, skin within the ear comes into contact with the electrodes. The head of the user conducts electricity between the electrodes whereby application of the earphone at the ear can be detected.

However, since the devices are intended to be used by any ordinary user, it is considered uncertain that detection of application is ensured since any of the electrodes may have poor contact with tissue of user. It is therefore a further desire to provide gear that provides a more reliable detection while it is still easy to use by an ordinary user.

SUMMARY

The present invention is based on the understanding that an ordinary user is comfortable with using earphones, and that addition of a microphone in an earphone can be used for acquiring sounds from which measurements on sounds present at the earphone. From the acquired sounds, detection can be made to determine whether the earphone is applied at the user's ear.

According to a first aspect, there is provided an apparatus comprising an earpiece and a signal processor. The earpiece is suitable to be applied at an auditory opening of a user's ear. The earpiece comprises a speaker enabled to be supplied with an audio signal for rendering, and a microphone arranged in vicinity of the speaker to acquire a sound signal from sounds present inside the auditory opening when the earpiece is applied at the ear. The signal processor is arranged to determine whether the earpiece is applied at the user's ear by analysis of the acquired sound signal comprising any of a sound signal component of an in-ear sound type present when the earpiece is applied or an outside-ear sound type present when the earpiece is not applied.

The in-ear sound type signal component may comprise a physiological sound signal. The physiological sound signal may comprise a signal component associated with breathing sounds of the user. The physiological sound signal may comprise a signal component associated with heart beat sounds of the user. The signal processor may be arranged to extract the heartbeat by low pass filtering the physiological sound signal in a low pass filter to detect a heart beat signal. The low pass filter may have a cutoff frequency between 3 and 10 Hz, preferably between 3 and 5 Hz, preferably 4 Hz.

The outside-ear sound type may comprise ambient noise, and the signal processor may be arranged to determine the earpiece not be applied when ambient noise sounds exceeds a threshold level. The threshold level may be determined by measurement of actual ambient noise by another microphone associated with the earpiece and arranged to always acquire a sound signal from sounds present outside the auditory opening.

The signal processor may be arranged to subtract the audio signal from the sound signal to provide the sound signal component.

The apparatus may further comprise an application arranged to control features of the application based on the determination whether the earpiece is applied or not. The application may be arranged to interrupt rendering associated with the audio signal when the earpiece is determined to not be applied, and arranged to resume the rendering when the earpiece is determined to be applied. Alternatively, or additionally, the application may be arranged to establish communication associated with the audio signal when the earpiece is determined to be applied, and arranged to terminate the communication when the earpiece is determined to not be applied.

The analysis may be based on any of frequency characteristics and periodicity of the acquired sound signal.

According to a second aspect, there is provided a method suitable for an apparatus comprising an earpiece suitable to be applied at a user's ear for rendering an audio signal in the user's ear when the earpiece is applied at the ear. The method comprises acquiring a sound signal by a microphone of the earpiece arranged in vicinity of the speaker to acquire the sound signal from sounds present in an auditory opening of the ear of the user when the earpiece is applied at the ear; and determining whether the earpiece is applied at the user's ear by analyzing of the acquired sound signal comprising any of a sound signal component of an in-ear sound type present when the earpiece is applied or an outside-ear sound type present when the earpiece is not applied.

The in-ear sound type signal component may comprise a physiological sound signal. The physiological sound signal may comprise a signal component associated with breathing sounds of the user, and the determining may comprise determining that the earpiece is applied when breathing sounds are detectable. The physiological sound signal may comprise a signal component associated with heart beat sounds of the user, and the determining may comprise determining that the earpiece is applied when heart beat sounds are detectable. The method may further comprise extracting the heartbeat by low pass filtering the physiological sound signal in a low pass filter to provide a heart beat signal. The low pass filter may have a cutoff frequency between 3 and 10 Hz, preferably between 3 and 5 Hz, preferably 4 Hz.

The outside-ear sound type may comprise ambient noise, and the determining may comprise determining that the earpiece is not applied when ambient noise sounds exceeds a threshold level. The method may further comprise determining the threshold by measurement of actual ambient noise outside the auditory opening by another microphone associated with the earpiece.

The method may further comprise subtracting the audio signal from the sound signal to provide the sound signal component.

The method may further comprise controlling features of an application based on the determination. The method may further comprise interrupting rendering associated with the audio signal when the earpiece is determined to not be applied; and resuming the rendering when the earpiece is determined to be applied. The method may additionally, or alternatively further comprise establishing communication associated with the audio signal when the earpiece is determined to be applied; and terminating the communication when the earpiece is determined to not be applied.

The analyzing may be based on any of frequency characteristics and periodicity of the acquired sound signal.

According to a third aspect, there is provided a computer readable medium comprising program code comprising instructions which when executed by a processor is arranged to cause the processor to perform the method according to the second aspect.

The instruction may be adapted to cause supplying an audio signal to a speaker of an earpiece suitable to be applied at a user's ear for rendering the audio signal in the user's ear when the earpiece is applied at the ear; acquiring a sound signal by a microphone of the earpiece arranged in vicinity of the speaker to acquire the sound signal from sounds present in an auditory opening of the ear of the user when the earpiece is applied at the ear; and determining whether the earpiece is applied at the user's ear by analysis of the acquired sound signal comprising any of a sound signal component of an in-ear sound type present when the earpiece is applied or an outside-ear sound type present when the earpiece is not applied.

The in-ear sound type signal component may comprise a physiological sound signal. The physiological sound signal may comprise a signal component associated with breathing sounds of the user, and the instructions for determining may comprise instructions for determining that the earpiece is applied when breathing sounds are detectable. The physiological sound signal may comprise a signal component associated with heart beat sounds of the user, and the instructions for determining may comprise instructions for determining that the earpiece is applied when heart beat sounds are detectable. The computer program may further comprise instructions for extracting the heart beat by low pass filtering the physiological sound signal in a low pass filter to provide a heart beat signal. The computer program may further comprise instructions to arrange the low pass filter to have a cutoff frequency between 3 and 10 Hz, preferably between 3 and 5 Hz, preferably 4 Hz.

The outside-ear sound type may comprise ambient noise, and the instructions for determining may comprise instructions for determining that the earpiece is not applied when ambient noise sounds exceeds a threshold level. The computer readable medium may further comprise instructions for determining the threshold by measurement of actual ambient noise outside the auditory opening by another microphone associated with the earpiece.

The computer program may further comprise instructions for subtracting the audio signal from the sound signal to provide the sound signal component.

The computer program may further comprise instructions for controlling features of an application based on the determination. The computer program may further comprise instructions for interrupting rendering associated with the audio signal when the earpiece is determined to not be applied; and resuming the rendering when the earpiece is determined to be applied.

The computer program may further comprise instructions for establishing communication associated with the audio signal when the earpiece is determined to be applied; and terminating the communication when the earpiece is determined to not be applied.

The instructions may be adapted to make the analysis be based on any of frequency characteristics and periodicity of the acquired sound signal.

According to a fourth aspect, there is provided an apparatus comprising two earpieces suitable to be applied at auditory openings of a user's ear, each earpiece comprising a microphone arranged to acquire a sound signal from sounds present inside the auditory opening when the earpiece is applied at the ear; a signal processor, wherein the signal processor is arranged to determine whether each earpiece is applied at the user's ear by analysis of the acquired sound signal comprising any of a sound signal component of an in-ear sound type present when the earpiece is applied or an outside-ear sound type present when the earpiece is not applied; and an application arranged to control a machine based on the determination whether the earpieces are applied or not.

BRIEF DESCRIPTION OF DRAWINGS

FIG. 3 schematically illustrates a computer readable medium.

DETAILED DESCRIPTION

Figure 1:
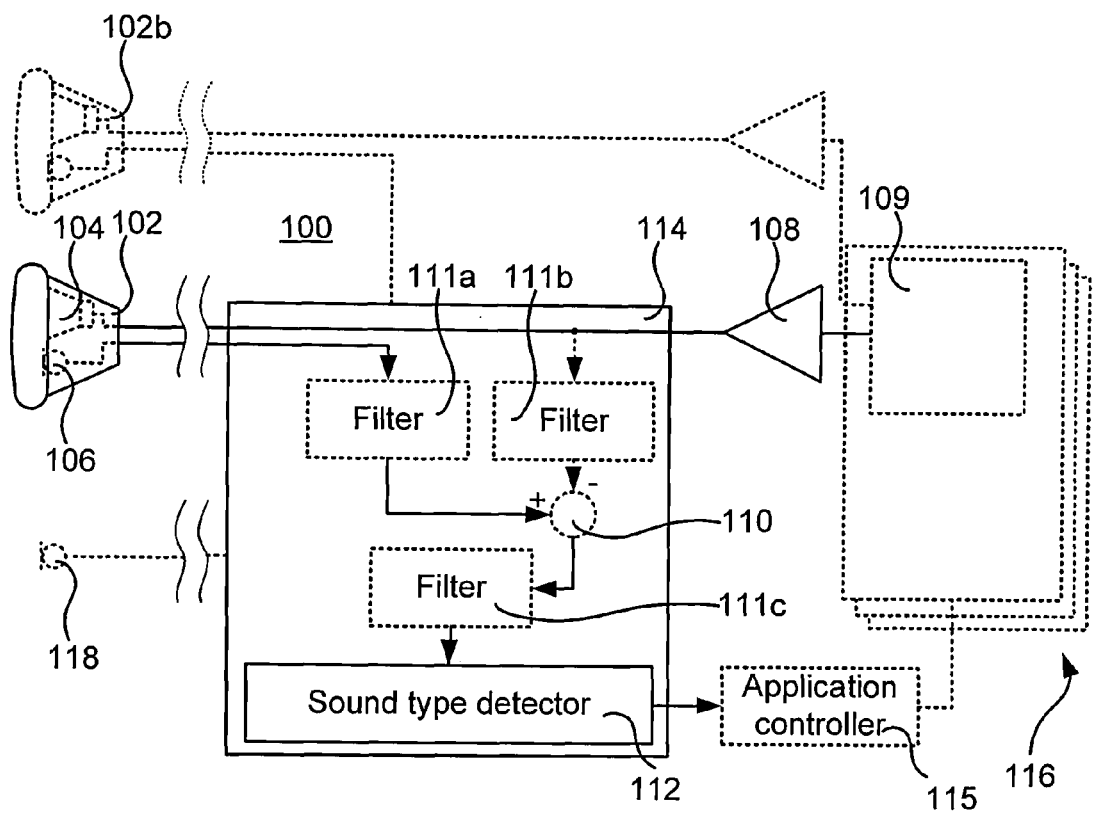
FIG. 1 schematically illustrates an apparatus according to an embodiment.

FIG. 1 schematically illustrates an apparatus 100 according to an embodiment. The apparatus 100 comprises a speaker arrangement 102, i.e. an earpiece arranged to be applied at an auditory opening of a user's ear, having a speaker 104 and a microphone 106 arranged together with the speaker 104. The speaker 104 is provided with an audio signal, e.g. music or speech, which preferably is provided by an amplifier 108, which in turn may get the audio content from an application element 109, e.g. a media player or audio output of a telephone. The microphone 106, which is arranged to acquire sounds present in the auditory opening of the ear, e.g. heart or breathing sounds and of course the audio sound generated by the speaker 104 when the earpiece is applied at the ear, or acquire ambient noise when not applied, can provide its output signal to an optional subtractor 110, which subtracts the audio signal from the microphone signal. Further optionally, the microphone signal is filtered by a filter 111a. In addition, or alternatively, the audio sound provided by amplifier 108 may be filtered by a filter 111b before input to the optional subtractor 110. The output from the optional subtractor 110 essentially comprises a heart and/or breathing sound signal when the earpiece is applied, and ambient noise when not applied since the signal components emanating from the audio sound are deleted. The heart and/or breathing sound signal or ambient noise signal is provided to a sound type detector 112. Here, it should be noted that a filter 111c can be arranged between the subtractor 110 and the sound type detector 112 instead of, or in addition to, the filter 111a between the microphone 106 and the subtractor 110 and/or the filter 111b between the amplifier 108 and the subtractor 110.

The sound type detector 112, which preferably is implemented by a signal processor 114, is arranged to determine whether the earpiece is applied at the user's ear. This is done by analysis of the acquired sound signal which is input to the sound type detector 112. The sound signal can comprise any of a sound signal component of an in-ear sound type present when the earpiece is applied or an outside-ear sound type present when the earpiece is not applied. Which one of these that is present, or at least dominant, can be determined by detecting certain sounds. For example, if physiological sounds, such as breathing sounds or heart beat sounds, are present, the sound type detector 112 will determine that the sound type is of in-ear type, i.e. the earpiece 102 is applied, or if ambient noise is dominant, the sound type detector 112 will determine that the sound type is of outside-ear type, i.e. the earpiece is not applied at the ear.

The subtractor 110, the optional filter(s) 111a, b, c, and the sound type detector 112 can be part of the signal processor 114 performing the functions of the elements 110, 111(a, b, c), 112, for example in analog or digital domain.

Detection of breathing sound is performed by identifying sound characteristics which the breathing has when the air is flowing in the head, and which breathing sound can be acquired by the microphone 106 when the earpiece 102 is applied.

By nature, the heartbeat produces a weak sound in the head of the user with frequency components mainly corresponding to the heart rate. The sound signal acquired by the microphone 106 can be amplified, filtered and processed to enable detection of the heart beat sounds. The filtering can comprise low-pass filtering, since the heartbeat itself normally is within the range of 0.5 to 3 Hz. Since sound provided by the speaker 104 normally is very low at these frequencies, a narrow filter can enhance the heart sound signal significantly.

Ambient noise, i.e. sounds present in the environment of the user or else where the apparatus 100 is present, is attenuated, by the earpiece 102 covering the auditory opening of the user's ear, before reaching the microphone 106 when the earpiece 102 is applied. Thus, sound components of ambient noise is less when the earpiece 102 is applied compared to when not applied. Detection of outside-ear sound type can thus be determined from analysis of presence of ambient noise in the acquired sound signal. The determination can be made from changes in ambient noise level, i.e. observing application and detaching, respectively, of the earpiece, or comparing the ambient noise level with a threshold level. The threshold level can be based on experience, or be determined by measurement of actual ambient noise by another microphone 118, e.g. the another microphone 118 being associated with the earpiece 102, e.g. when part of a headset comprising the earpiece 102 and the another microphone 118, which is intended for input of speech from the user.

For example, in case both a high level of ambient noise and breathing sounds are present, the detection of ambient noise can be discriminated since the presence can be due to an extremely high ambient noise level, or that attenuation of the ambient noise is moderate and a relatively high amount of the ambient noise reaches the auditory opening of the ear although an earpiece is applied. However, the detection of breathing sounds is only likely to emanate from an applied earpiece. Detection of heart beat sounds, which are weaker by nature, is in turn regarded as a relatively certain sign of an applied earpiece. The signal type detector 112 is preferably arranged to make determinations as discussed above to find the dominant sound type also in regard of which sounds that can be present when, and not only on their sound level. For example, a ranking between the three sounds discussed above upon determination whether the earpiece is applied can be 1) heart beat, 2) breathing sound, 3) ambient noise.

Other sounds present in the head of a user and thus at the auditory opening of the ear can be speech with certain sound characteristics due to its propagation inside the head, chewing sounds, etc.

Analysis of the sound signal to detect breathing or heart beat sounds is preferably determined based on analysis of periodicity and/or frequency content of the sound signal.

The type of the sounds can also be determined based on their frequency properties, since high frequencies are normally attenuated more by tissue of the user than low frequencies. Thus, by observing acquired sound signal, preferably when any audio provided by the speaker 104 is subtracted by subtractor 110, and determining distribution over frequency, the sound type can be determined.

One or more of these determination techniques can be used for the determination. For example, the determination can be made from only one of detection of breathing sounds, heart beat sounds, ambient noise level, or frequency characteristics. The determination can also be made from any combination of these.

Based on the analysis of the sound type, i.e. whether the sound type is determined to be in-ear type or outside ear-type, and thus the determination whether the earpiece 102 is applied or not, an application controller 115 which is arranged to receive the result of the determination can control behavior of one or more applications 116. An application 116 can comprise the application element 109 arranged to output the audio content. One example on control of the application 116 can be routing audio related to music or incoming/outgoing calls to the earpiece 102 only when the earpiece is applied in the user's ear. Another example is to adjust ring tone volume to lower levels if it is detected that the earpiece 102 is applied in the user's ear since the apparatus then most probably is close to the user. Further another example is to enable input from another microphone 118 associated with the earpiece 102, e.g. when it is a part of a headset comprising the earpiece 102 and the another microphone 118, only when the earpiece 102 is applied. Still another example is to turn on a wireless headset comprising the earpiece 102 when the earpiece 102 is applied, or turn it off when not applied. Another example is to determine if mono or stereo audio is to be output to earpiece or earpieces 102, 102b depending on if one or two earpieces 102, 102b are applied. Here, when only one earpiece of the two is applied, the audio output is routed only to the earpiece applied. Further another example is call acceptance, i.e. picking up an incoming call, when the earpiece 102 is applied or upon application. Still another example is to start or resume audio rendering, e.g. from a media player upon application of the earpiece 102, and stopping or pausing when detaching the earpiece 102 from the ear. Any combination of these is of course possible for adapting to the nature of the application 116.

Here, it should be noted that the above demonstrated approach for determining if the earpiece 102 is applied can also be applicable for an earpiece without a speaker 104, such as an earplug for protection against harmful noise. For example, a noisy machine, such as a drilling or grinding machine, cannot be started unless ear protectors are applied. Preferably, logic circuitry for enabling the starting of the machine is arranged to enable starting only if both ears are protected by earpieces 102. Of course, the ear protectors can be provided with speaker 104 as well, and any of the other features elucidated above can be combined with this embodiment.

Figure 2:
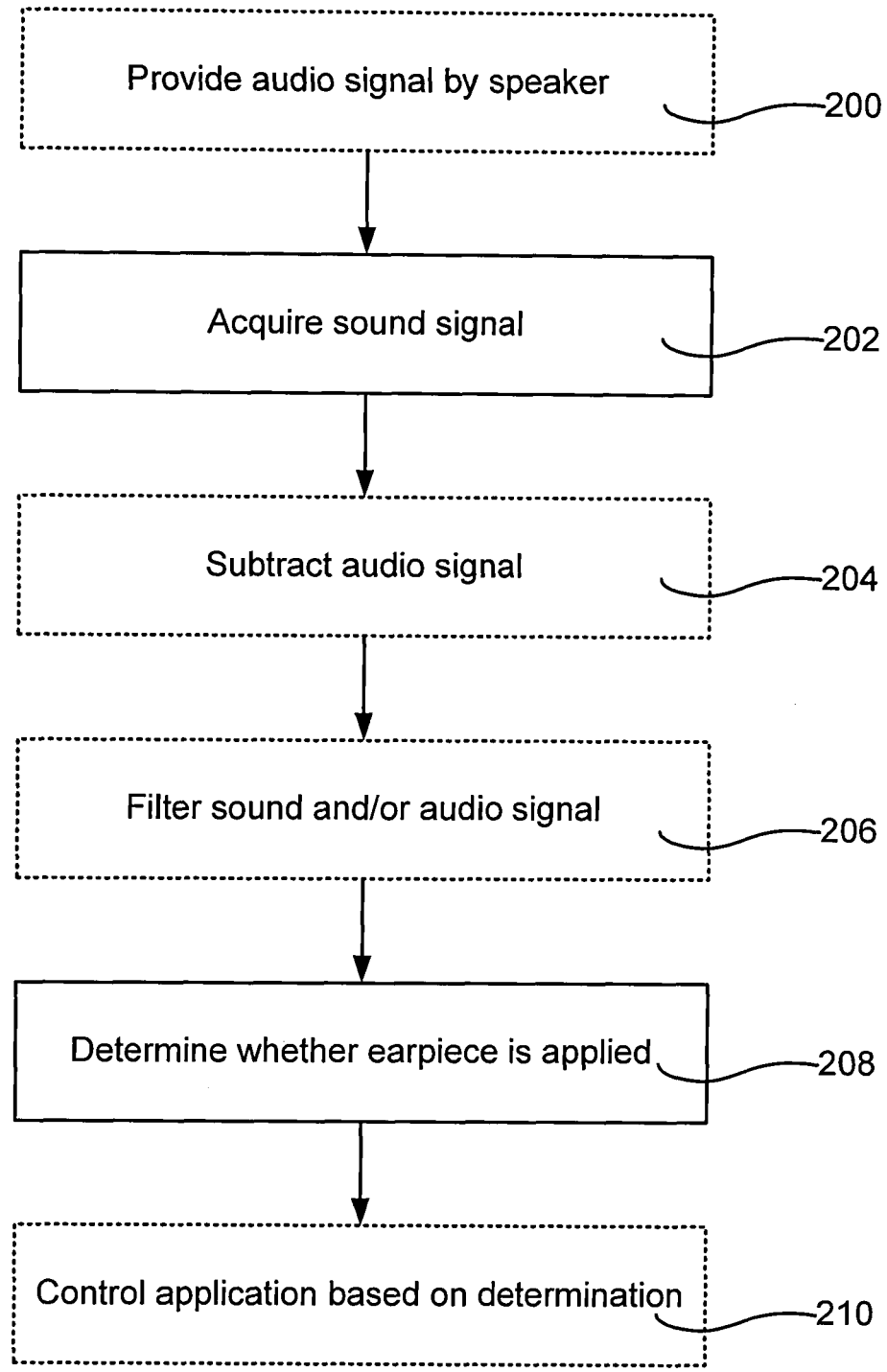
FIG. 2 is a flow chart illustrating a method according to an embodiment.

FIG. 2 is a flow chart illustrating a method according to an embodiment. The method is suitable for an earpiece to be applied at a user's ear for rendering an audio signal in the user's ear when the earpiece is applied at the ear, as demonstrated above with reference to FIG. 1. The method comprises a sound acquisition step 202 where sounds present in the auditory opening of the ear are acquired by a microphone, which is arranged to acquire, e.g. heart or breathing sounds when the earpiece is applied at the ear, or acquire ambient noise when not applied. The method further comprises a determination step 208 where it is determined whether the earpiece is applied at the user's ear. This is performed by analysis of the acquired sound signal regarding comprising of any of a sound signal component of an in-ear sound type present when the earpiece is applied or an outside-ear sound type present when the earpiece is not applied. This can be performed as demonstrated with reference to FIG. 1.

The method can comprise an audio provision step 200 where an audio signal is rendered by a speaker of the earpiece. The provided audio signal will be highly present in the acquired sound signal. Therefore, the audio signal, which is known, can be subtracted from the acquired sound signal in an audio subtracting step 204. Further optionally, the acquired sound signal or the audio signal can be filtered before any subtraction, or the sound signal after the subtraction can be filtered in a signal filtering step 206.

Based on the determination of whether the earpiece is considered to be applied or not, one or more applications can be controlled in an application control step 210. The controlling can for example comprise interrupting rendering associated with the audio signal based on the determination when the earpiece is determined to not be applied, and resuming the rendering when the earpiece is determined to be applied. Another example is establishing communication associated with the audio signal based on the determination when the earpiece is determined to be applied, e.g. picking up a telephone call, and terminating the communication when the earpiece is determined to not be applied, e.g. hanging up.

An example of an in-ear sound type signal component is a physiological sound signal, such as breathing or heart beat sounds. When these are determined to be present, it is very likely that the user has applied the earpiece. Extracting the heartbeat can be made by low pass filtering the physiological sound signal in a low pass filter to provide a heart beat signal. The low pass filter preferably has a cutoff frequency between 3 and 10 Hz, preferably between 3 and 5 Hz, preferably 4 Hz, since the main frequency, i.e. the heart beat itself, is limited in frequency by its nature.

An example on outside-ear sound type is ambient noise, and the earpiece is determined to not be applied when ambient noise sounds exceeds a for example a threshold level. The threshold level can be determined as demonstrated with reference to FIG. 1.

The demonstrated approach is particularly suitable for an earpiece of closed type.

The methods according to the present invention are suitable for implementation with aid of processing means, such as computers and/or processors. Therefore, there is provided computer programs, comprising instructions arranged to cause the processing means, processor, or computer to perform the steps of any of the methods according to any of the embodiments described with reference to FIG. 2, in the apparatus. The computer programs preferably comprises program code which is stored on a computer readable medium 300, as illustrated in FIG. 3, which can be loaded and executed by a processing means, processor, or computer 302 to cause it to perform the methods, respectively, according to embodiments of the present invention, preferably as any of the embodiments described with reference to FIG. 2. The computer 302, which can be present in the apparatus as illustrated in FIG. 1, and computer program stored on the computer readable medium 300 can be arranged to execute the program code sequentially where actions of the any of the methods are performed stepwise, or be performed on a real-time basis, where actions are taken upon need and availability of needed input data. The processing means, processor, or computer 302 is preferably what normally is referred to as an embedded system. Thus, the depicted computer readable medium 300 and computer 302 in FIG. 3 should be construed to be for illustrative purposes only to provide understanding of the principle, and not to be construed as any direct illustration of the elements.

The invention claimed is:

1. An apparatus comprising
an earpiece suitable to be applied at an auditory opening of a user's ear, the earpiece comprising
a speaker enabled to be supplied with an audio signal for generating sound, and
a microphone arranged in vicinity of the speaker to acquire a sound signal from sounds present inside the auditory opening when the earpiece is applied at the ear;
a signal processor, wherein the signal processor is arranged to determine whether the earpiece is applied at the user's ear by analysis of the acquired sound signal comprising any of a sound signal component of an in-ear sound type present when the earpiece is applied or an outside-ear sound type present when the earpiece is not applied, the signal processor being arranged to determine a distribution over frequency of the acquired sound signal to determine whether the earpiece is applied at the user's ear;
the in-ear sound type signal component comprising a physiological sound signal, wherein the physiological sound signal comprises a signal component associated with heart beat sounds of the user; and
the signal processor comprising a low pass filter being arranged to extract the heart beat sounds by low pass filtering the physiological sound signal in the low pass filter to detect a heart beat signal.

2. The apparatus according to claim 1, wherein the physiological sound signal further comprises a signal component associated with breathing sounds of the user.

3. The apparatus according to claim 1, wherein the low pass filter has a cutoff frequency between 3 and 10 Hz, preferably between 3 and 5 Hz, preferably 4 Hz.

4. The apparatus according to claim 1, wherein the outside-ear sound type comprises ambient noise, and the signal processor is arranged to determine the earpiece not being applied when ambient noise sound exceeds a threshold level.

5. The apparatus according to claim 4, wherein the threshold level is determined by measurement of ambient noise by another microphone associated with the earpiece and arranged to always acquire a sound signal from sounds present outside the auditory opening.

6. The apparatus according to claim 1, wherein the signal processor is arranged to subtract the audio signal from the sound signal to provide the sound signal component.

7. The apparatus according to claim 1, further comprising an application controller arranged to control features of an application based on the determination whether the earpiece is applied or not.

8. The apparatus according to claim 7, wherein the application controller is arranged to interrupt the application generating sound associated with the audio signal when the earpiece is determined to not be applied, and arranged to resume the application generating sound when the earpiece is determined to be applied.

9. The apparatus according to claim 7, wherein the application controller is arranged to control the application establishing communication associated with the audio signal when the earpiece is determined to be applied, and arranged to control the application terminating the communication when the earpiece is determined to not be applied.

10. The apparatus according to claim 1, wherein the analysis is based on any of frequency characteristics and periodicity of the acquired sound signal.

11. A method, for an apparatus comprising an earpiece suitable to be applied at a user's ear for outputting an audio signal in the user's ear when the earpiece is applied at the ear, comprising acquiring a sound signal by a microphone of the earpiece arranged in vicinity of a speaker to acquire the sound signal from sounds present in an auditory opening of the ear of the user when the earpiece is applied at the ear;

determining whether the earpiece is applied at the user's ear by analyzing of the acquired sound signal comprising any of a sound signal component of an in-ear sound type present when the earpiece is applied or an outside-ear sound type present when the earpiece is not applied, the analyzing comprising determining a distribution over frequency of the acquired sound signal to determine whether the earpiece is applied at the user's ear;

the in-ear sound type signal component comprising a physiological sound signal, wherein the physiological sound signal comprises a signal component associated with heart beat sounds of the user;

extracting the heart beat sounds by low pass filtering the physiological sound signal in a low pass filter to detect a heart beat signal; and the determining comprises determining that the earpiece is applied when heart beat sounds are detectable.

12. The method according to claim 11, wherein the physiological sound signal further comprises a signal component associated with breathing sounds of the user, and the determining comprises determining that the earpiece is applied when breathing sounds are detectable.

13. The method according to claim 11, wherein the low pass filter has a cutoff frequency between 3 and 10 Hz, preferably between 3 and 5 Hz, preferably 4 Hz.

14. The method according to claim 11, wherein the outside-ear sound type comprises ambient noise, and the determining comprises determining that the earpiece is not applied when ambient noise sound exceeds a threshold level.

15. The method according to claim 14, further comprising determining the threshold by measurement of ambient noise outside the auditory opening by another microphone associated with the earpiece.

16. The method according to claim 11, further comprising subtracting the audio signal from the sound signal to provide the sound signal component.

17. The method according to claim 11, further comprising controlling features of an application based on the determination.

18. The method according to claim 17, further comprising
interrupting outputting sound associated with the audio signal when the earpiece is determined to not be applied; and
resuming the outputting sound when the earpiece is determined to be applied.

19. The method according to claim 17, further comprising
establishing communication associated with the audio signal when the earpiece is determined to be applied; and
terminating the communication when the earpiece is determined to not be applied.

20. The method according to claim 11, wherein the analyzing is based on any of frequency characteristics and periodicity of the acquired sound signal.

21. A non-transitory computer readable medium comprising program code comprising instructions which when executed by a processor is arranged to cause the processor to perform supplying an audio signal to a speaker of an earpiece suitable to be applied at a user's ear for outputting the audio signal in the user's ear when the earpiece is applied at the ear;

acquiring a sound signal by a microphone of the earpiece arranged in vicinity of the speaker to acquire the sound signal from sounds present in an auditory opening of the ear of the user when the earpiece is applied at the ear;

determining whether the earpiece is applied at the user's ear by analysis of the acquired sound signal comprising any of a sound signal component of an in-ear sound type present when the earpiece is applied or an outside-ear sound type present when the earpiece is not applied, the analysis comprising determining a distribution over frequency of the acquired sound signal to determine whether the earpiece is applied at the user's ear;

the in-ear sound type signal component comprising a physiological sound signal, wherein the physiological sound signal comprises a signal component associated with heart beat sounds of the user;

instructions for extracting the heart beat sounds by low pass filtering the physiological sound signal in a low pass filter to provide a heart beat signal; and the instructions for determining comprises instructions for determining that the earpiece is applied when heart beat sounds are detectable.

22. The computer readable medium according to claim 21, wherein the physiological sound signal further comprises a signal component associated with breathing sounds of the user, and the instructions for determining comprises instructions for determining that the earpiece is applied when breathing sounds are detectable.

23. The computer readable medium according to claim 21, wherein the low pass filter has a cutoff frequency between 3 and 10 Hz, preferably between 3 and 5 Hz, preferably 4 Hz.

24. The computer readable medium according to claim 21, wherein the outside-ear sound type comprises ambient noise, and the instructions for determining comprises instructions for determining that the earpiece is not applied when ambient noise sound exceeds a threshold level.

25. The computer readable medium according to claim 24, further comprising instructions for determining the threshold by measurement of ambient noise outside the auditory opening by another microphone associated with the earpiece.

26. The computer readable medium according to claim 22, further comprising instructions for subtracting the audio signal from the sound signal to provide the sound signal component.

27. The computer readable medium according to claim 21, further comprising instructions for controlling features of an application based on the determination.

28. The computer readable medium according to claim 27, further comprising instructions for
interrupting outputting sound associated with the audio signal when the earpiece is determined to not be applied; and
resuming the outputting sound when the earpiece is determined to be applied.

29. The computer readable medium according to claim 27, further comprising instructions for
establishing communication associated with the audio signal when the earpiece is determined to be applied; and
terminating the communication when the earpiece is determined to not be applied.

30. The computer readable medium according to claim 21, wherein the analysis is based on any of frequency characteristics and periodicity of the acquired sound signal.

31. An apparatus comprising two earpieces suitable to be applied at auditory openings of a user's ear, each earpiece comprising a microphone arranged to acquire a sound signal from sounds present inside the auditory opening when the earpiece is applied at the ear;

a signal processor, wherein the signal processor is arranged to determine a distribution over frequency of the acquired sound signal to determine whether each earpiece is applied at the user's ear by analysis of the acquired sound signal comprising any of a sound signal component of an in-ear sound type present when the earpiece is applied or an outside-ear sound type present when the earpiece is not applied; and a controller arranged to control a machine based on the determination whether the earpieces are applied or not.

* * * * *